United States Patent
Hoogeboom

[11] Patent Number: 5,803,649
[45] Date of Patent: Sep. 8, 1998

[54] LOCKING MECHANISM

[76] Inventor: Thomas J. Hoogeboom, 7544 Oak Shore South, Portage, Mich. 49024-7850

[21] Appl. No.: 749,108

[22] Filed: Nov. 14, 1996

Related U.S. Application Data

[60] Provisional application No. 60/006,722 Nov. 14, 1995.

[51] Int. Cl.[6] ............................................. B25G 3/12
[52] U.S. Cl. ...................... 403/325; 403/321; 403/374; 403/109; 81/320; 81/325; 606/142
[58] Field of Search ........................... 606/142, 143, 606/208; 81/319, 320, 324, 325, 322, 323; 403/320, 319, 316, 315, 353, 355, 376, 325, 321, 261, 265, 374, 109, 377

[56] References Cited

U.S. PATENT DOCUMENTS

| | | |
|---|---|---|
| 546,380 | 9/1895 | Olton . |
| 567,193 | 9/1896 | Nash . |
| 600,864 | 3/1898 | Glover . |
| 1,804,420 | 5/1931 | Kelley ................................ 403/353 X |
| 3,615,114 | 10/1971 | Harris . |
| 3,989,394 | 11/1976 | Ellis .................................. 403/320 X |
| 4,549,544 | 10/1985 | Favaron ................................ 606/143 |
| 4,858,608 | 8/1989 | McQuilkin ............................ 606/142 |
| 5,048,150 | 9/1991 | Guerin . |
| 5,282,817 | 2/1994 | Hoogeboom et al. ............. 606/208 X |
| 5,354,313 | 10/1994 | Boebel . |
| 5,417,203 | 5/1995 | Tovey et al. . |

*Primary Examiner*—Anthony Knight
*Assistant Examiner*—William L. Miller
*Attorney, Agent, or Firm*—Price,Heneveld,Cooper, DeWitt & Litton

[57] ABSTRACT

A locking mechanism useful in various microsurgical, laproscopic and endoscopic surgical instruments includes a lock body which is linearly movable between a locked and an unlocked position, and a plate having a slot through which a linkage rod or the like passes. The slot includes a larger diameter portion through which a linkage rod or the like can freely pass when the lock body is in the unlocked position, and a relatively narrow section which restricts or prevents movement of the rod in one direction when the lock body is in the locked position. The slotted plate is free to pivot between an angle wherein the linkage rod is engaged by the edges of the narrow portion of the slot and thus wedged against movement, and a second angle wherein the rod is not engaged by the edges of the narrow portion of the slot, wherein by linkage rod can be moved through the lock body in one direction, but not in the opposite direction.

3 Claims, 4 Drawing Sheets

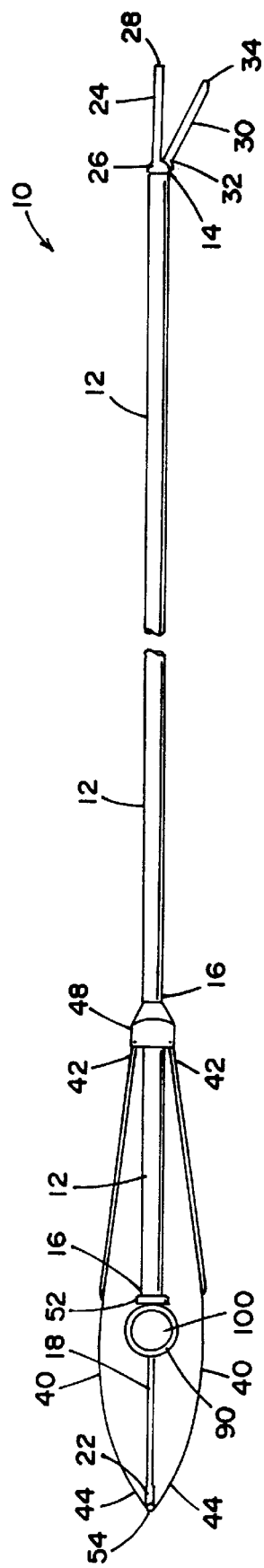
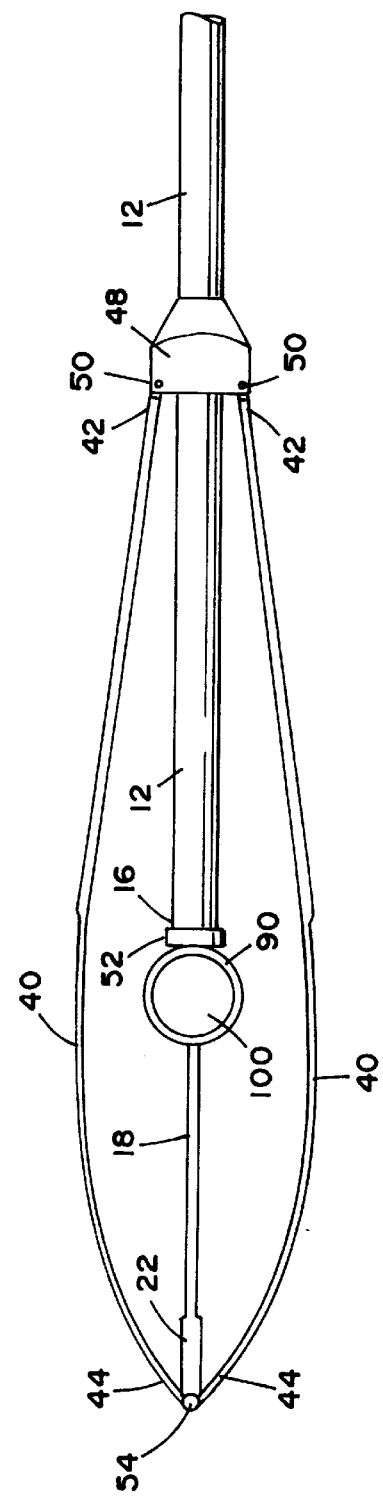
FIG. 1
FIG. 2

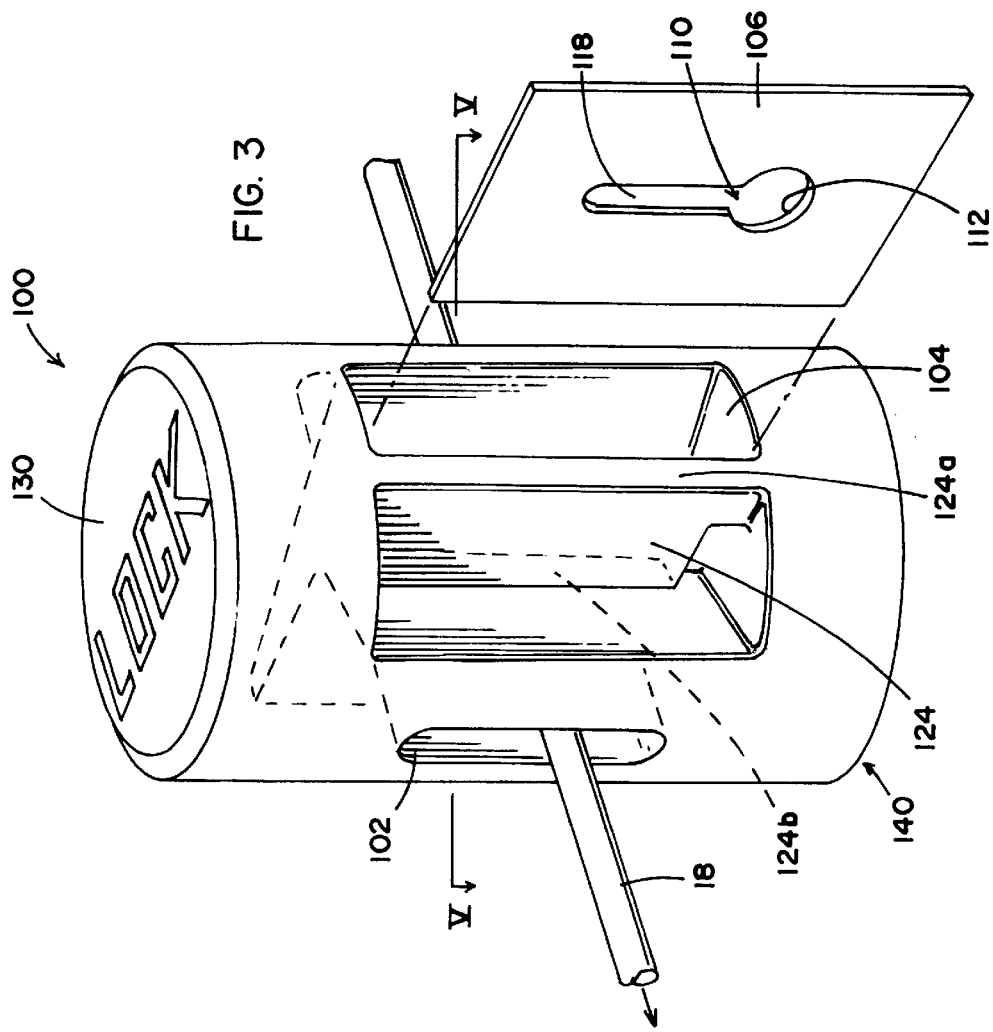
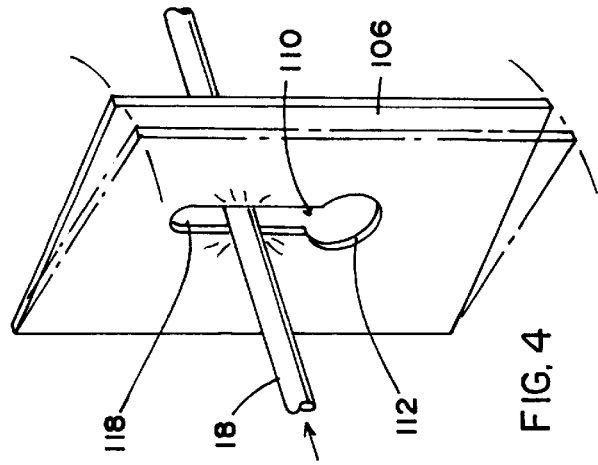
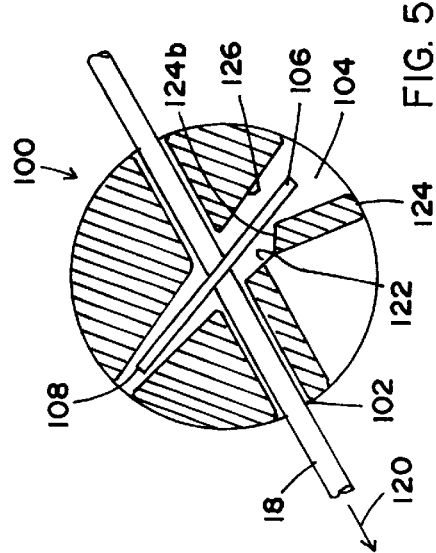

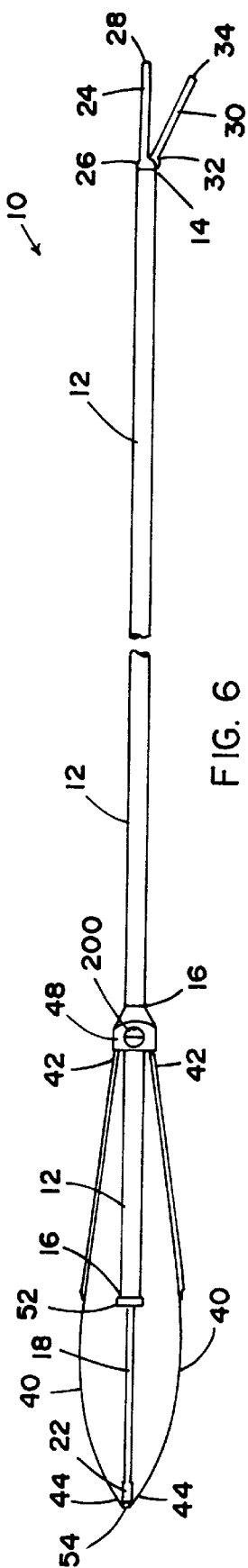
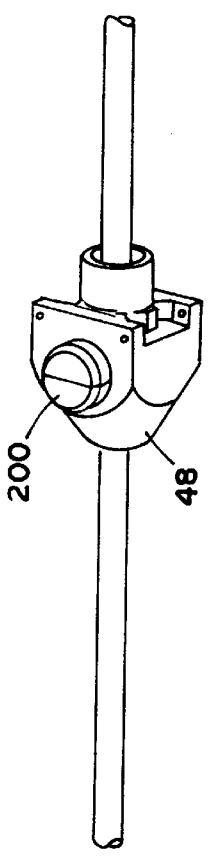
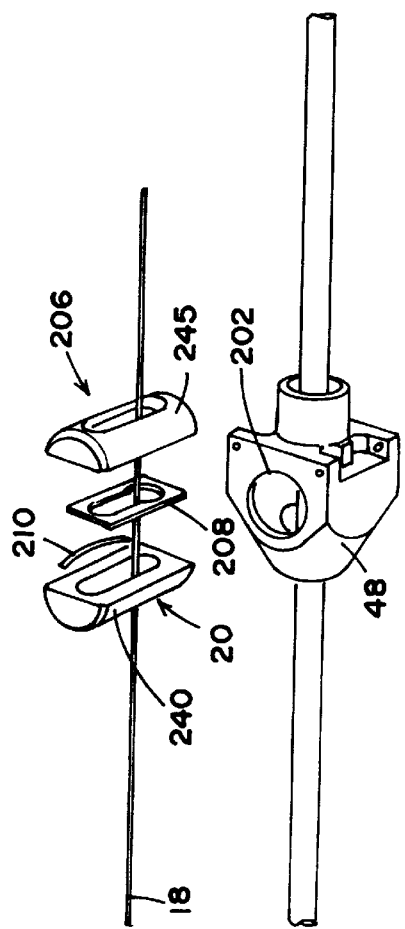
FIG. 6
FIG. 7
FIG. 8

LOCKING MECHANISM

This application claims the benefit of U.S. Provisional Application No. 60/006,722, entitled "LOCKING MECHANISM", filed Nov. 14, 1995.

BACKGROUND OF THE INVENTION

This invention relates to a locking mechanism for releasably retaining a movable linkage rod or the like in a fixed position.

Delicate surgical operations such as microsurgery, laproscopic surgery and endoscopic surgery often require surgical instruments having clamps, scissors, jaws, blades, grippers or other end effectors located at the end of a long, relatively narrow extension rod which provides access to tissue within the body with minimum disturbance of adjacent tissue. Such instruments must provide precise control over the end effectors through the use of control elements at the handle end of the instrument which can be easily and precisely manipulated with the fingers of an operator.

Known instruments for microsurgery, laproscopic surgery and endoscopic surgery have generally comprised an extension rod having an end effector attached at one end of the rod and the handle affixed to the other end of the extension rod. With the known surgical instruments, the opposed members such as jaws, grippers or the like can be controlled by an actuator mechanism located at or near the handle portion of the instrument. While the opposed members of the end effector can generally be positioned at any angle between a fully opened and a fully closed position by appropriate manipulation of the actuator mechanism, it is generally difficult to manually hold the opposed members of the end effector in a desired angular relationship for an extended period of time. Known instruments have not generally included any means for locking or holding the opposed members of the end effector in a desired angular relationship between the opened and closed positions.

SUMMARY OF THE INVENTION

The invention provides a locking mechanism which is broadly applicable to a variety of devices having a linkage rod wherein it is desirable to temporarily lock the rod in a selected position. The invention is particularly useful for use in various microsurgical, laproscopic and endoscopic surgical instruments, particularly clamping or gripping type instruments having an end effector with opposed gripping or clamp members, at least one of which is translatable or rotatable with respect to the other.

The locking mechanism is comprised of a lock body which is linearly movable between a locked and an unlocked position, and a plate having a slot through which a linkage rod or the like passes. The slot includes a larger diameter portion through which a linkage rod or the like can freely pass when the lock body is in the unlocked position, and a relatively narrow section which restricts or prevents movement of the rod in one direction when the lock body is in the lock position. The slotted plate is free to pivot between an angle wherein the linkage rod is engaged by the edges of the narrow portion of the slot and thus wedged against movement, and a second angle (which is generally orthogonal to the linkage rod) wherein the rod is not engaged by the edges of the narrow portion of the slot, whereby the linkage rod can be moved through the lock body in one direction, but not in the opposite direction.

BRIEF DESCRIPTION OF THE DRAWINGS

FIG. 1 is a side view of a surgical instrument utilizing the locking mechanism of the invention.

FIG. 2 is an enlarged side view of the handle area of the instrument shown in FIG. 1.

FIG. 3 is an exploded perspective view of the locking mechanism of the invention showing the slotted plate removed from the lock body, and showing a linkage rod passing through the lock body.

FIG. 4 is a perspective view showing a linkage rod passing through the slotted plate.

FIG. 5 is a cross-sectional view as seen along lines V—V of FIG. 3.

FIG. 6 is a side view of a surgical instrument utilizing a second embodiment of the locking mechanism.

FIG. 7 is an enlarged perspective view of the handle end piece 48 and the locking mechanism 200 disposed therein.

FIG. 8 is an exploded perspective view showing the components comprising the locking mechanism shown in FIG. 7 and illustrating the manner in which the locking mechanism is assembled.

DESCRIPTION OF THE PREFERRED EMBODIMENT

Figure 9:
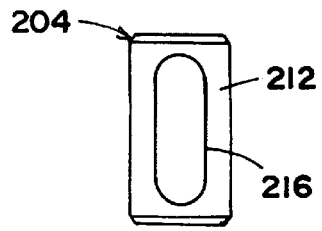
FIG. 9 is a front elevational view of the distal half of the lock body shown in FIG. 8.

While the instrument is capable of being utilized in various devices having a linkage rod or the like, wherein it is desirable to temporarily lock the rod in a selected position, the invention will be illustrated with reference to an endoscopic surgical instrument shown in FIGS. 1 and 2.

The surgical instrument 10 includes a movable jaw 30 and a fixed jaw 24 located at the end of sleeve 12. Squeezing the resiliently flexible actuating handles 40 together produces displacement of rod 18 slidably positioned within sleeve 12, which is joined to and thus causes movable jaw 30 to pivot. Movable jaw 30 can be locked in a selected fixed position relative to jaw 24 by locking linkage rod 18 (which passes through tube 12 and connects to jaw 30) to prevent movement thereof with respect to tube 12. This is achieved with locking mechanism 100 shown in FIG. 3 mounted at the end 52 of sleeve 12.

With reference to FIG. 3, the illustrated lock 100 is generally barrel shaped and has an elongated opening 102 which passes radially through the lock 100. Lock 100 is slidably retained within housing 90 mounted on the end 52 of sleeve 12, for translational movement along the cylindrical axis between a locked positioned and an unlocked position. Lock 100 includes a wedge shaped recess 104 which is generally perpendicular to slot 102. Disposed within recess 104 is a wobble plate 106 which can pivot within recess 104, generally about a longitudinal axis at the end 108 of plate 106 which is nearest the narrow end of slot 104 (FIG. 5). Wobble plate 106 includes an approximately key shaped slot 110 having a circular portion 112 through which linkage rod 18 can freely pass in either direction, and a narrow, elongate portion 118 through which rod 18 can pass in only the direction indicated by arrow 120.

Lock 100 can be positioned in the locked position (as shown in FIG. 4), wherein rod 18 passes through elongate portion 118 of slot 110, or in the unlocked position (not shown), wherein rod 18 passes through circular portion 112 of slot 110. Lock 100 can be moved from the unlocked position to the locked position by pushing on top surface 130, or moved from the locked position to the unlocked position by pushing lock 100 upwardly by applying pressure to the underside 140.

Lock 100 is preferably made of plastic, and includes an integrally molded spring 124. Spring 124 is a molded plastic wall which has a fixed edge 124a which extends along side of and defines one edge of the wide end of opening 104. It has a free end 124b which projects into opening 104. Spring 124 is slightly resiliently flexible.

When lock 100 is in the locked position, and rod 18 is forcibly moved in the direction indicated by arrow 120, plate 106 can pivot toward wall 122 of recess 104 into a position which is substantially perpendicular to rod 18, whereby rod 18 can pass through narrow slot 118. Flexible spring wall 124 yields sufficiently to insure the absence of wedging between rod 18 and slot 118. When forces are no longer imposed upon rod 18, integral spring 124 urges plate 106 into a central position of recess 104 (as shown in the cross-sectional view of FIG. 5), wherein rod 18 is wedged between the edges of narrow portion 118 of slot 110, and is locked into a fixed position relative to lock 100. If rod 18 is forcibly urged in the direction opposite of the direction indicated by arrow 120, plate 106 pivots toward wall 126, wherein rod 18 becomes tightly wedged between the edges of the narrow portion 118 of slot 106.

Figure 10:
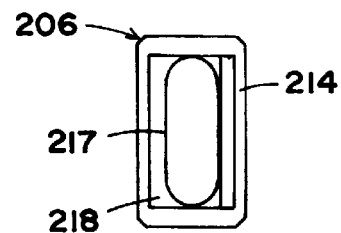
FIG. 10 is a front elevational view of the proximal half of the lock body shown in FIG. 8.
Figure 11:
FIG. 11 is a horizontal cross sectional view of the distal half of the lock body.
Figure 12:
FIG. 12 is a horizontal cross sectional view of the proximal half of the lock body.

In FIG. 6 there is shown a surgical instrument employing a locking mechanism 200 for releasably holding a linkage rod 18 in a fixed position. The primary difference between locking mechanism 100 (shown in FIGS. 1–5) and locking mechanism 200 (shown in FIGS. 6–13) is that the locking mechanism is located within an end piece 48 at the distal end of the handle portion of the instrument. FIG. 7 shows an exploded perspective view of the end piece 48 of the handle portion of instrument 10 with locking mechanism 200 disposed within a bore through end piece 48. The various components of the locking mechanism are shown in FIG. 8. Handle end piece 48 serves as a housing for the locking mechanism 200 and also functions to guide rod 12 through the locking mechanism 200. The bore 202 in handle end piece 48 preferably extends all the way through the handle end piece. Locking mechanism 200 includes a distal lock body half 204, a proximal lock body half 206, a lockplate 208, and a leaf spring 210. Referring to FIGS. 9–12, the lock body halves each have a semi-cylindrical shape with flat seating or mating surfaces 212 and 214. When mating surfaces 212 and 214 are brought together as shown in FIG. 7, the lock body halves 204 and 206 together form a substantially cylindrically shaped lock body. Each of the lock body halves 204 and 206 includes an oblong aperture or opening 216 and 217 respectively. The openings 216 and 217 extend through the lock body halves 204 and 206 respectively along a direction generally perpendicular to the seating surfaces 212 and 214. Referring to FIGS. 10 and 12, lock body half 206 includes a recess 218 which increases in depth from one side of the lock body half 206 to the other side, to define a wedge shaped volume 219 (FIG. 12).

Figure 13:
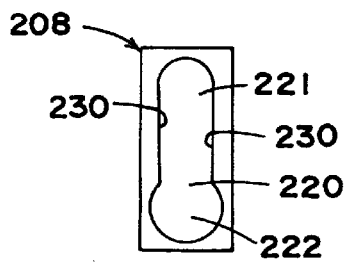
FIG. 13 is a front elevational view of the lockplate shown in FIG. 9.
Figure 14:
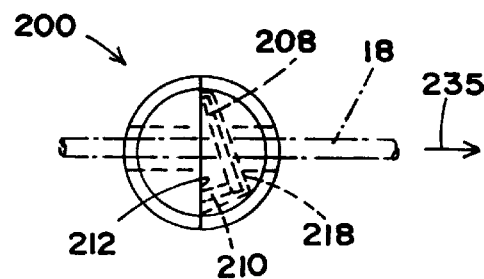
FIG. 14 is a transverse cross sectional view through the assembled locking mechanism 200.

Referring to FIG. 13, lockplate 208 is a generally rectangular shaped plate having an oblong opening 220 having a narrow portion 221 and a wide portion 222. Opening 220 has a key-hole shape. Lockplate 208 has a width which is greater than the width of the openings 216 and 217 through lock body halves 204 and 206 respectively. However, the width of the lockplate is less than the width of the recess 218 so that lockplate 208 can be disposed within the wedge shaped volume 219 and can pivot between a position wherein the lockplate is urged against the recess wall 218 by spring 210 so that the edges 230 along the narrow portion 221 of opening 220 engage rod 18 and prevent it from being drawn through the locking mechanism 200 in the direction indicated by arrow 235, and a position wherein lockplate 208 is urged toward surface 212 against spring 210 whereby the edges 230 of the narrow portion 221 of opening 220 do not engage rod 18 and allow free axial movement of the rod through opening 220. Spring 210 normally biases the lockplate 208 into a orientation wherein the edges of the opening 220 in lockplate 208 normally engage the rod 18 to prevent axial movement of the rod through the opening when the rod extends through the narrow portion 221 of the opening. This allows rod 18 to be easily moved in an axial direction opposite to the direction indicated by arrow 235 while preventing movement of rod 18 in the axial direction indicated by arrow 235. Lock mechanism 200 is assembled by inserting lockplate 208 into the recess 218 of the proximal lock body half 206 positioning leaf spring 210 over lockplate 208 and bringing the two lock body halves 204 and 206 together as shown in FIG. 14. Thereafter, the assembly is inserted into bore 202 and rod 18 is inserted through opening 216 of distal lock body half 204, through opening 220 in lockplate 208 disposed within the lock body halves, and through opening 217 in lock body half 206. The outer cylindrical surfaces 240 and 245 of lock body halves 204 and 206 are configured and sized so that the assembly (including the two lock body halves) forms a generally cylindrically shaped locking mechanism which fits tightly within bore 202, such that frictional engagement between the outer cylindrical walls 240 and 245 and the inner walls of cylindrical bore 202 is sufficient to prevent inadvertent movement of the locking mechanism 200 along the axis of the cylindrical locking mechanism. Thus, the frictional engagement between the locking mechanism and the bore 202 prevents inadvertent movement of the locking mechanism, and hence the lockplate 208, between the locked position wherein the rod 18 extends through the narrow portion 221 of lockplate 208 and an unlocked position wherein the rod 18 extends through the wide portion 222 of opening 220 in lockplate 208.

While the foregoing describes use of the locking mechanism in the field of surgery, the invention may find appropriate uses in other applications requiring a small, simple locking device. Of course, it is understood that the foregoing describes the preferred embodiment of the invention, and that various changes and alterations can be made without departing from the spirit in broader aspects of the invention.

The embodiments of the invention in which an exclusive property or privilege is claimed are defined as follows:

1. A locking mechanism for releasably holding a rod in a fixed position, comprising:
   a rod;
   a lock body slidably retained in a housing, the rod extending through the lock body; and
   a lockplate being disposed in the lock body and having an elongate opening through which the rod extends, the opening having a width which varies along the length of the opening, the lockplate being linearly movable with the lock body when the lock body is slid within the housing, the linear movement being between a first position in which the rod extends through a narrow portion of the opening and a second position in which the rod extends through a wide portion of the opening, the lockplate being pivotally movable within the lock body between a first orientation wherein the edges of the opening engage the rod to prevent axial movement of the rod through the opening when the rod extends through the narrow portion of the opening, and a second orientation wherein the edges of the opening do not engage the rod to allow free axial movement of the rod through the opening when the rod extends through the narrow portion of the opening, the wide portion of the opening being sufficiently wide so that the edges of the opening will not engage the rod when the rod extends through the wide portion of the opening irrespective of the pivotal orientation of the lockplate.

2. The locking mechanism of claim 1, further comprising a spring which is operably connected to the lock body and which normally biases the lockplate into the first pivotal orientation whereby the edges of the opening normally engage the rod to prevent axial movement of the rod through the opening when the rod extends through the narrow portion of the opening.

3. The locking mechanism of claim 1 in combination with a surgical instrument having distal and proximal ends, the housing for the lock body is defined on the proximal end of the surgical instrument, and the rod controls an end effector on the distal end.

* * * * *